(12) United States Patent
Perrey et al.

(10) Patent No.: US 12,070,354 B2
(45) Date of Patent: Aug. 27, 2024

(54) METHODS AND SYSTEM FOR DETECTING MEDICAL IMAGING SCAN PLANES USING PROBE POSITION FEEDBACK

(71) Applicant: General Electric Company, Schenectady, NY (US)

(72) Inventors: Christian Fritz Perrey, Mondsee (AT); Stephan Anzengruber, Pramet (AT)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 373 days.

(21) Appl. No.: 16/162,285

(22) Filed: Oct. 16, 2018

(65) Prior Publication Data

US 2020/0113542 A1 Apr. 16, 2020

(51) Int. Cl.
*A61B 8/00* (2006.01)
*A61B 8/08* (2006.01)
*A61B 34/20* (2016.01)
*G06N 20/00* (2019.01)

(52) U.S. Cl.
CPC .......... *A61B 8/4254* (2013.01); *A61B 8/5207* (2013.01); *A61B 34/20* (2016.02); *A61B 8/483* (2013.01); *A61B 2034/2055* (2016.02); *A61B 2034/2063* (2016.02); *G06N 20/00* (2019.01)

(58) Field of Classification Search
CPC ..... A61B 8/4254; A61B 34/20; A61B 8/5207; A61B 2034/2063; A61B 2034/2055; A61B 8/483; A61B 2034/105; A61B 2034/2065; A61B 8/145; A61B 8/4444; A61B 8/4461; A61B 8/4483; A61B 8/5215; A61B 8/54; A61B 8/58; G06N 20/00
See application file for complete search history.

(56) References Cited

U.S. PATENT DOCUMENTS

| | | | |
|---|---|---|---|
| 8,303,502 B2 * | 11/2012 | Washburn | A61B 8/145 600/437 |
| 10,964,424 B2 | 3/2021 | Pagoulatos et al. | |
| 2014/0153358 A1 * | 6/2014 | Balakrishnan | A61B 8/463 367/7 |
| 2016/0328998 A1 * | 11/2016 | Pedersen | A61B 8/4245 |
| 2017/0086785 A1 * | 3/2017 | Bjaerum | A61B 8/13 |
| 2017/0360403 A1 * | 12/2017 | Rothberg | A61B 8/52 |
| 2018/0153505 A1 * | 6/2018 | Cadieu | A61B 8/4254 |
| 2018/0225993 A1 * | 8/2018 | Buras | A61B 34/20 |
| 2018/0240551 A1 | 8/2018 | Perrey et al. | |

OTHER PUBLICATIONS

Yaqub, M. et al., "A Deep Learning Solution for Automatic Fetal Neurosonographic Diagnostic Plane Verification Using Clinical Standard Constraints," Ultrasound in Medicine and Biology, vol. 43, No. 12, Dec. 2017, Published Online Sep. 28, 2017, 9 pages.

* cited by examiner

*Primary Examiner* — Boniface N Nganga
(74) *Attorney, Agent, or Firm* — McCoy Russell LLP

(57) ABSTRACT

Various methods and systems are provided for automatically detecting scan planes of anatomical structures and providing guidance for obtaining target views during an imaging procedure. As one example, a method includes outputting to a user, instructions for navigating a medical imaging probe from a current scan position to a next scan position for obtaining a desired scan plane of a target anatomical structure based on received image data of the target anatomical structure and position data, the position data obtained from a position sensor on the probe, during receiving the image data.

20 Claims, 7 Drawing Sheets

METHODS AND SYSTEM FOR DETECTING MEDICAL IMAGING SCAN PLANES USING PROBE POSITION FEEDBACK

FIELD

Embodiments of the subject matter disclosed herein relate to medical imaging and automatic detection of target scan planes and/or anatomical structures within acquired images.

BACKGROUND

Medical imaging procedures, such as ultrasound imaging procedures, involve a user moving an imaging probe (e.g., ultrasound transducer) over or within a patient in order to obtain images of target anatomical structures (such as organs). Multiple image views, obtained from specific scan planes at the target anatomical structure, may be required for proper medical diagnosis of the patient. Additionally, different measurements may be required at the different image views. Image data acquired at the different image views may be used to generate images used by a medical professional for medical diagnosis. Some systems for analyzing the generated images include machine learning and/or deep learning frameworks which involve various algorithms that define an initial model based on training data. The frameworks automatically adjust the initial model based on user feedback. Conventional frameworks cover a broad range of applications, such as organ detection, scan plane selection, segmentation and tissue classification.

BRIEF DESCRIPTION

In one embodiment, a method comprises outputting to a user, instructions for navigating a medical imaging probe from a current scan position to a next scan position for obtaining a desired scan plane of a target anatomical structure based on received image data of the target anatomical structure and position data, the position data obtained from a position sensor on the probe, during receiving the image data.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The following description relates to various embodiments of classifying acquired diagnostic medical images and guiding a user of an imaging system in acquiring images of target scan planes of anatomical structures based on image data and position data acquired by an imaging probe. In one example, a medical diagnostic system (MDS) may include an ultrasound imaging system, such as the MDS shown in FIG. 1B. The ultrasound imaging system includes an imaging probe (e.g., ultrasound transducer) that is moved and guided around a patient via a user. During an imaging procedure, the imaging probe acquires image data used to generate images of the patient, as the probe is moved in space. The probe may additionally include a position sensor and position data may be acquired along with and corresponding to the acquired image data. A controller of the MDS may be configured to analyze the acquired images and position data to classify the images and identify images showing target scan planes of anatomical structures (organs, as one example) and/or target anatomical structures, using one or more models and algorithms stored in memory of the MDS, such as the memory of the MDS systems shown in FIGS. 1A-1B. The algorithms and/or models may include machine learning algorithms, anatomical structure models, and anatomical feature specific models, referred to herein as a scan plane and/or anatomical structure detection framework, that enable the controller to automatically detect target scan planes of anatomical structures, thereby producing desired image views that increase the accuracy of medical diagnosis based on the selected images. However, this detection framework alone may not provide assistance to more inexperienced users during an imaging procedure. For example, inexperienced users may miss desired views during an imaging procedure and/or may be unable to find desired views during the imaging procedure. This may result in improper diagnosis or an inability for a medical professional to make an accurate diagnosis based on the obtained image views. In particular, it may be difficult for a user to find a target scan plane and/or anatomical structure (such as the fetal heart) during an imaging procedure. Thus, position sensor data from the probe may be utilized to help the user find target scan planes during an imaging procedure (e.g., an ultrasound examination).

Figure 2A:
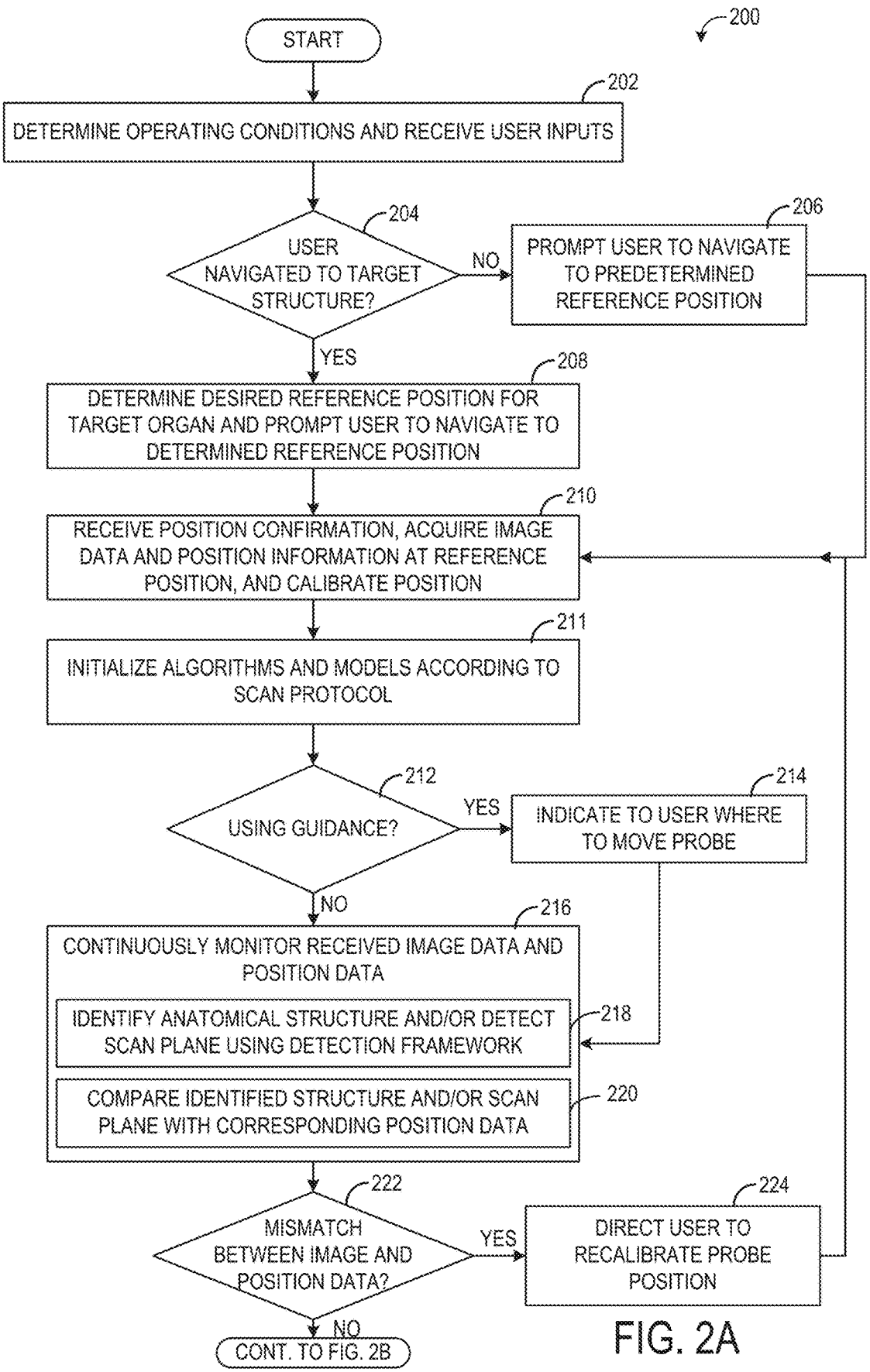
FIGS. 2A-2B show a method for classifying diagnostic medical images and guiding a user of an imaging system, during an imaging procedure, based on image data and position data acquired by a medical imaging probe, according to an embodiment of the invention.
Figure 2B:
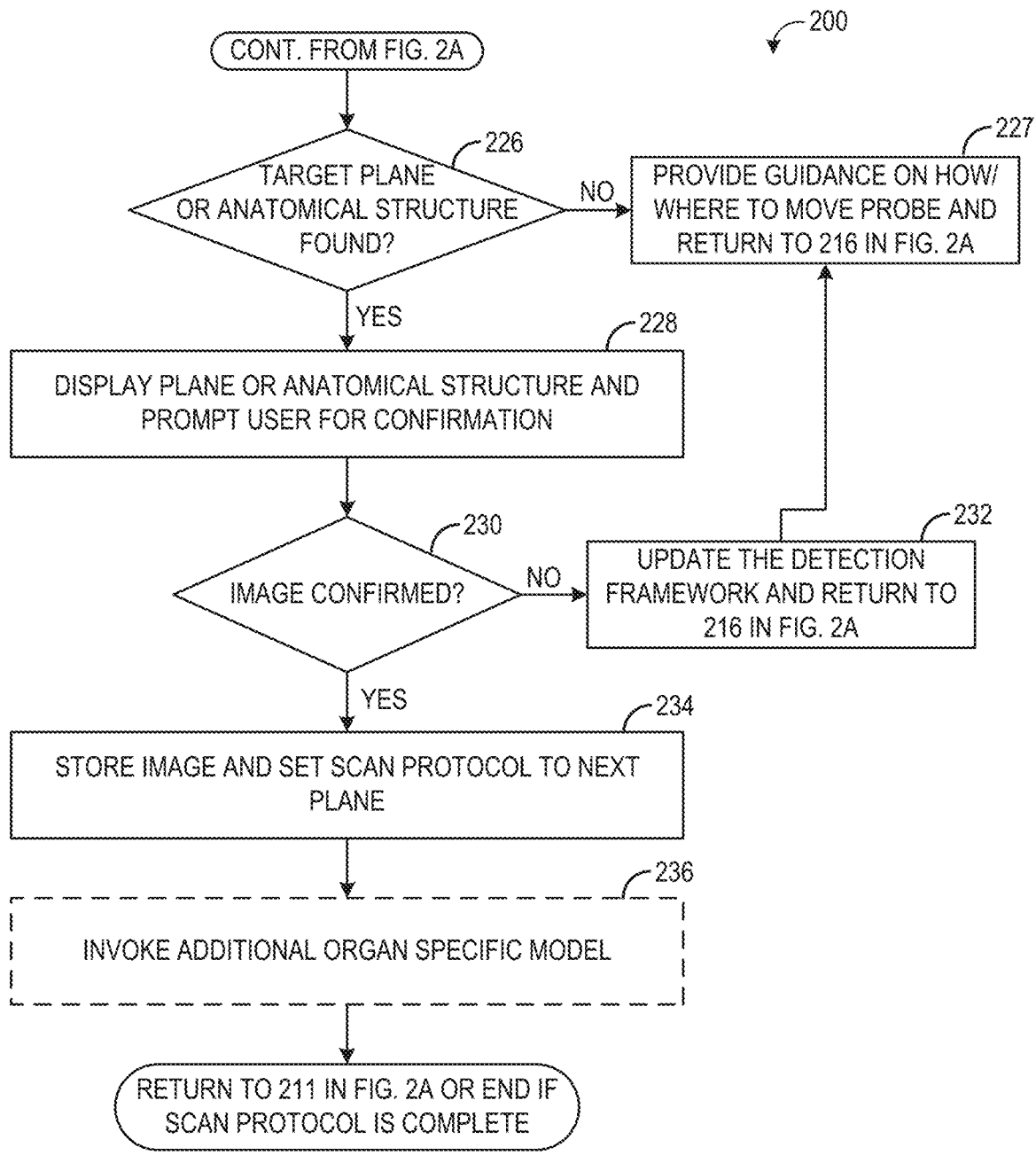
Figure 3:
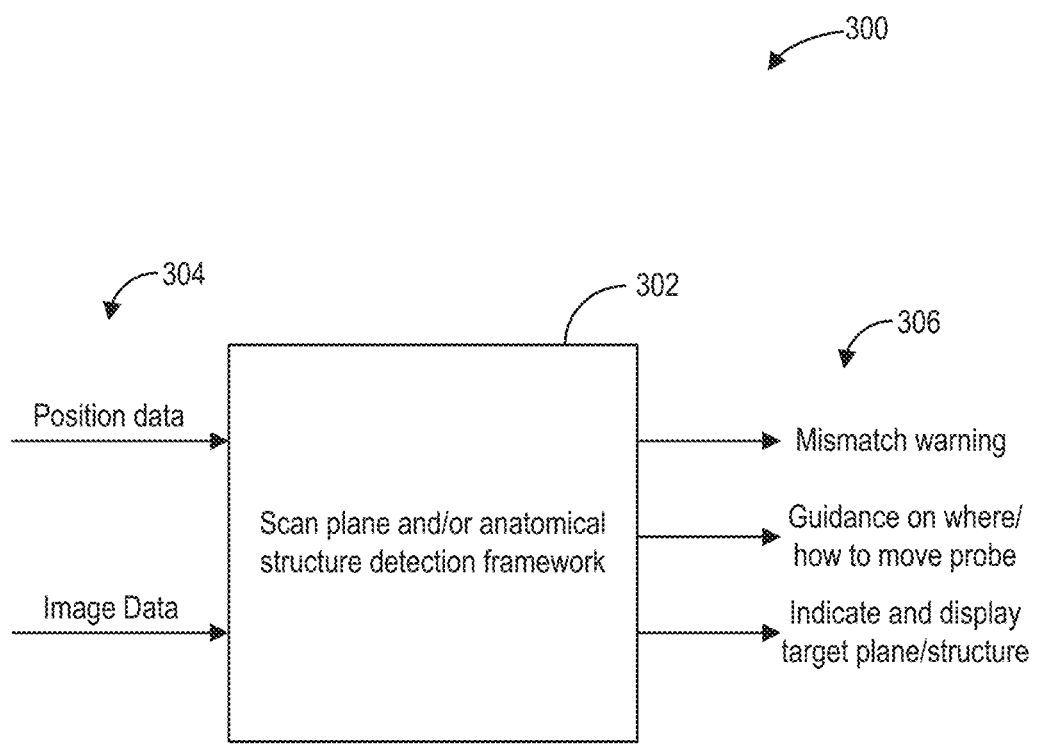
FIG. 3 shows an example block diagram of a scan plane and/or anatomical structure detection framework, according to an embodiment of the invention.

As shown in FIG. 3, along with image data, position data from the probe position sensor may also be used as an input into the scan plane and/or anatomical structure detection framework and the framework may output to the user (via a display, in one example) one or more of a mismatch warning when the classification based on the image data does not match the position data, guidance on where/how to move the probe to obtain a desired view or scan plane, and/or an indication and/or display of the image including the target plane/structure. As shown in the method presented at FIGS. 2A-2B, during an imaging procedure, image data and position data are simultaneously and continuously acquired via the probe and then input into the detection framework to identify scan planes and/or anatomical structures. If there is a mismatch between the scan plane or structure detected based on the image data and the corresponding position data, the system may output a mismatch warning and ask a user to recalibrate the position sensor (as shown in FIGS.

Figure 4A:
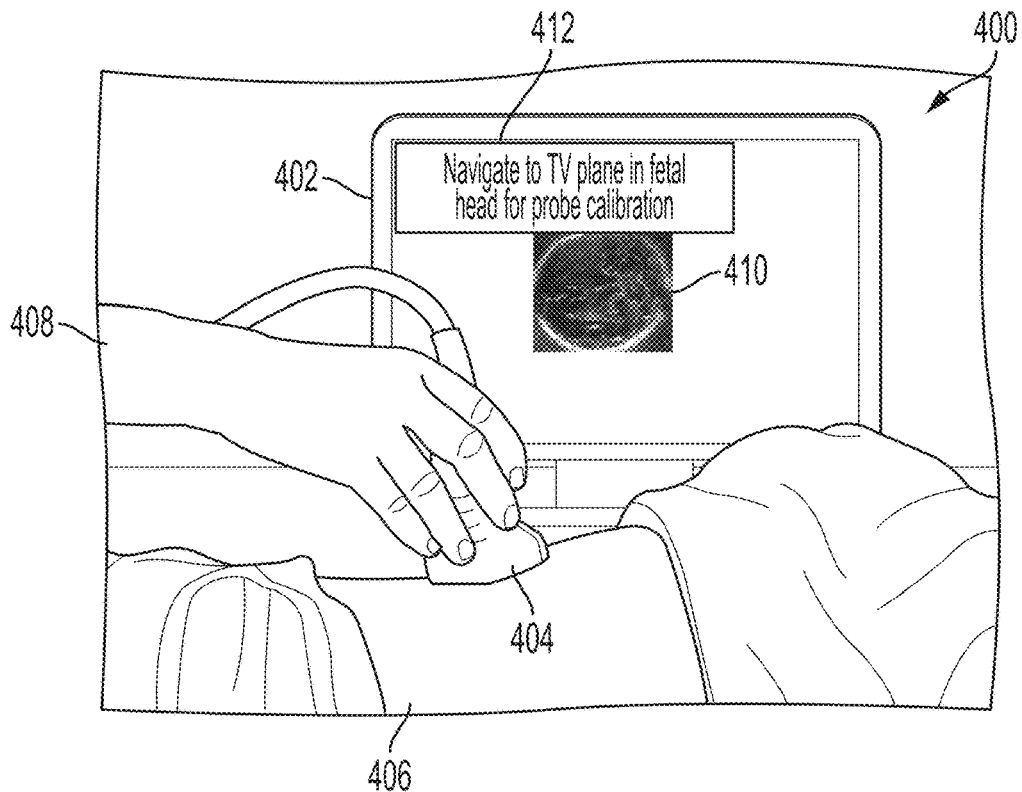
FIGS. 4A-4D show examples of different prompts displayed to a user of an ultrasound imaging system during an imaging procedure and the method presented at FIGS. 2A-2B, according to an embodiment of the invention.
Figure 4B:
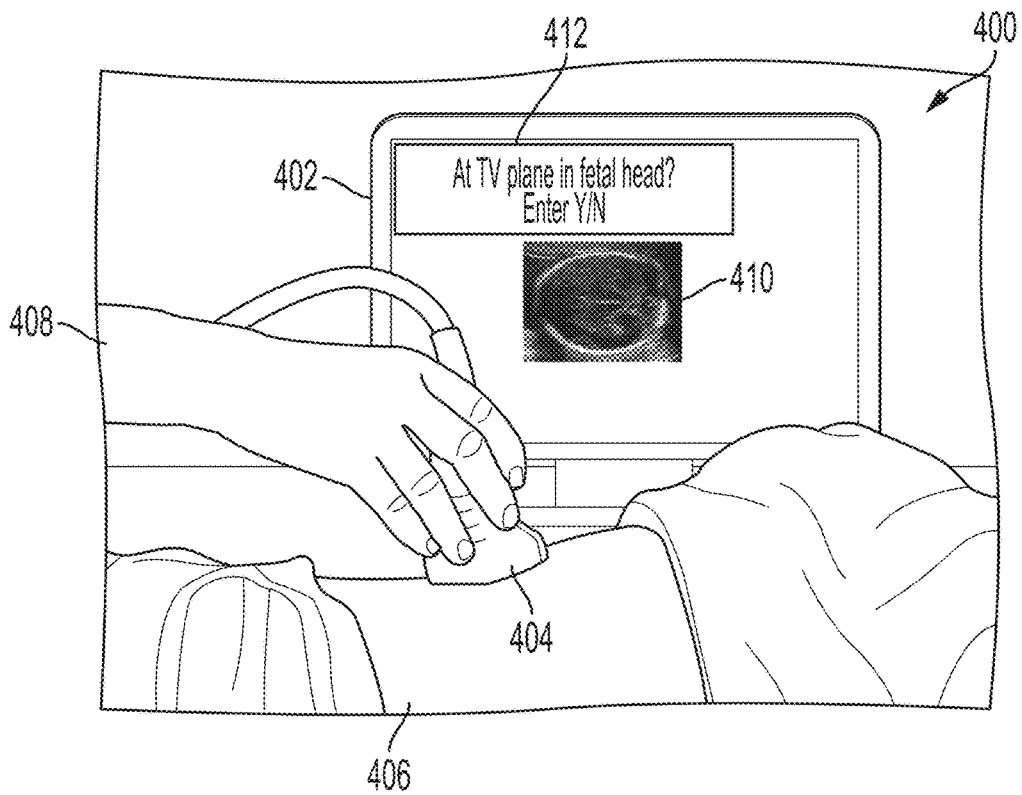

4A-4D). Additionally or alternatively, the position data may be used to update and or increase the accuracy of the target views identified by the detection framework. The system may also guide the user how/where to move the probe to get the next desired view in a scan protocol (as shown in FIGS. 4A-4B). In this way, obtaining desired image views during an imaging procedure may be made easier for a user, thereby increasing the quality of images acquired and increasing the accuracy of a medical diagnosis based on the resulting images.

Figure 1A:
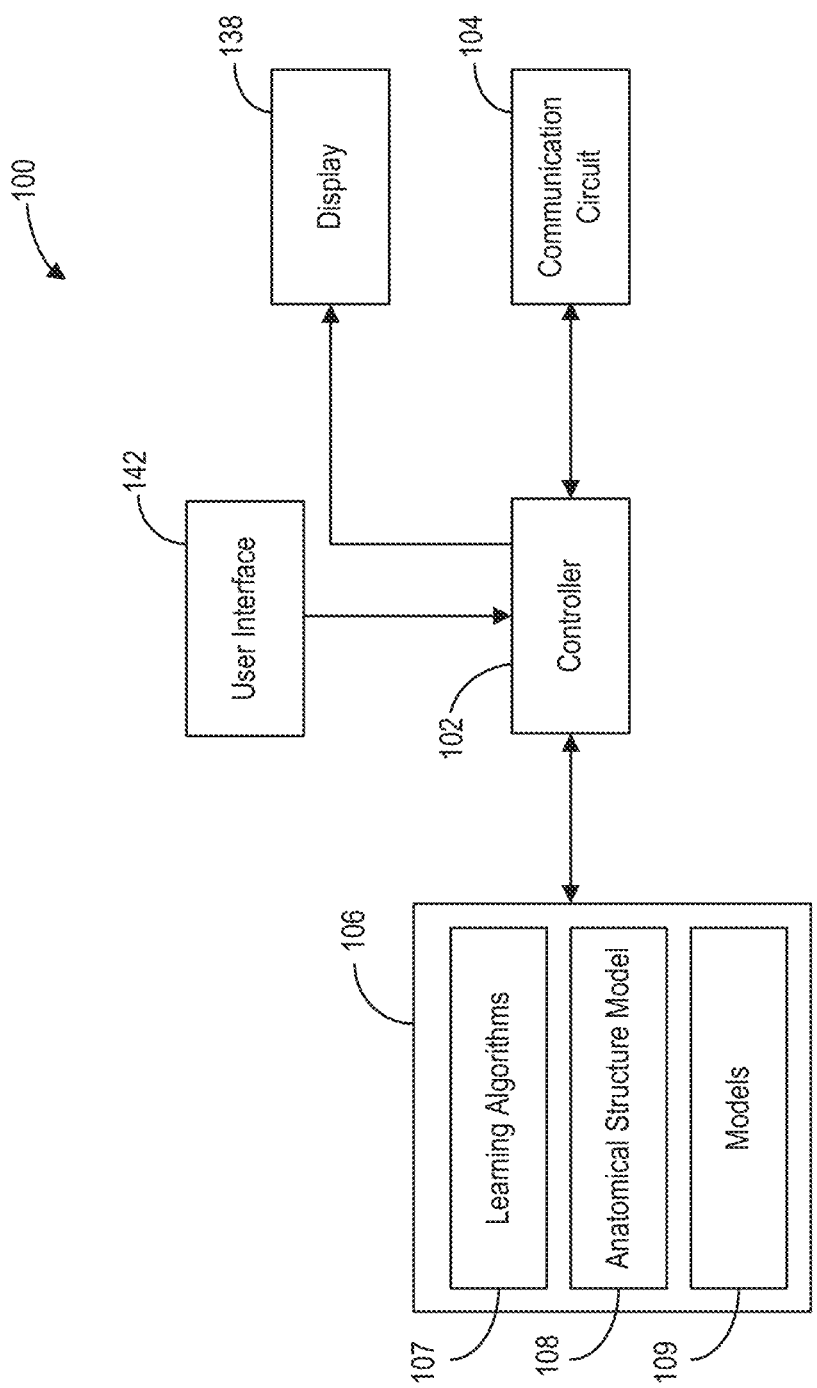
FIGS. 1A-1B show schematic diagrams of medical diagnostic systems, according to embodiments of the invention.
Figure 1B:
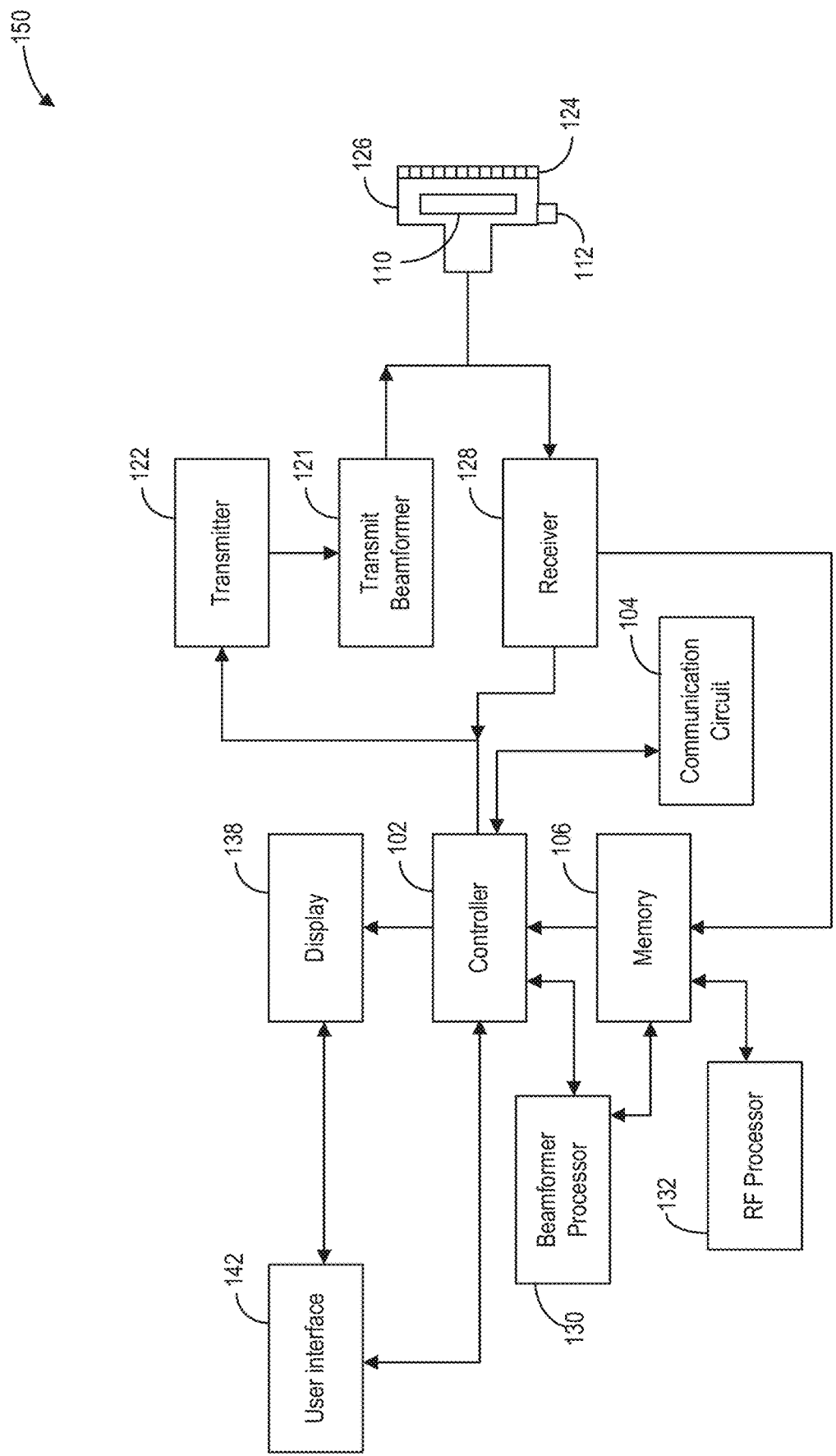

FIGS. 1A-1B illustrate schematic block diagrams of various embodiments of a medical diagnostic system (MDS) 100, 150. The MDS 100 of FIG. 1A includes a controller (e.g., controller circuit) 102 operably coupled to a communication circuit 104, a display (e.g., display device) 138, a user interface 142, and a memory 106.

The communication circuit 104 may be communicatively coupled to one or more alternative MDS (e.g., such as the MDS 150 shown in FIG. 1B), one or more medical diagnostic imaging systems, a remote server, and/or the like via corresponding bi-directional communication links. The one or more medical diagnostic imaging systems may include ultrasound imaging systems or devices, in one example. The remote server may be configured to store sets of medical images from prior scanning and/or clinician sessions of a patient acquired by the one or more medical diagnostic imaging systems.

The bi-directional communication links may be a wired (e.g., via a physical conductor) and/or wireless communication (e.g., utilizing radio frequency (RF)) link for exchanging data (e.g., data packets) between the MDS 100 and the alternative MDS, the one or more medical diagnostic imaging systems, the remote server, and/or the like. For example, the MDS 100 may receive a set of medical images from saved scanning and/or clinician sessions from the alternative MDS, the one or more medical diagnostic imaging systems, the remote server, and/or the like. The set of medical images may include medical imaging data used to generate the images and corresponding position sensor data from a probe used to acquire the medical imaging data, as discussed further herein. The bi-directional communication links may be based on a standard communication protocol, such as Ethernet, TCP/IP, WiFi, 802.11, a customized communication protocol, and/or the like.

The controller 102 is configured to control the operation of the MDS 100. The controller 102 may include one or more processors. Optionally, the controller 102 may include a central processing unit (CPU), one or more microprocessors, a graphics processing unit (GPU), or other electronic components capable of processing inputted data according to specific logical instructions stored on a memory of the controller or coupled with the controller. Optionally, the controller 102 may include and/or represent one or more hardware circuits or circuitry that include, are connected with, or that both include and are connected with one or more processors, controllers, and/or other hardware logic-based devices. Additionally or alternatively, the controller 102 may execute instructions stored on a tangible and non-transitory computer readable medium (e.g., the memory 106).

The controller 102 may be operably coupled to and/or control the communication circuit 104. The communication circuit 104 is configured to receive and/or transmit information with the one or more medical diagnostic imaging systems, the alternative MDS, the remote server, and/or the like. The communication circuit 104 may represent hardware that is used to transmit and/or receive data along the bi-directional communication links. The communication circuit 104 may include a transceiver, receiver, transceiver and/or the like and associated circuitry (e.g., antennas) for wired and/or wirelessly communicating (e.g., transmitting and/or receiving) with the one or more medical diagnostic imaging systems, the alternative MDS, the remote server, and/or the like. For example, protocol firmware may be stored in the memory 106, which is accessed by the controller 102. The protocol firmware provides the network protocol syntax for the controller 102 to assemble data packets, establish and/or partition data received along the bi-directional communication links, and/or the like.

The controller 102 is operably coupled to the display 138 and the user interface 142. The display 138 may include one or more liquid crystal displays (e.g., light emitting diode (LED) backlight), organic light emitting diode (OLED) displays, plasma displays, CRT displays, and/or the like. The display 138 may display patient information, one or more medical images and/or videos, components of a graphical user interface, one or more 2D, 3D, or 4D ultrasound image data sets from ultrasound data stored in the memory 106 or currently being acquired, measurements, diagnosis, treatment information, alerts or indications, directions, and/or the like received by the display 138 from the controller circuit 102.

The user interface 142 controls operations of the controller 102 and is configured to receive inputs from the user. The user interface 142 may include a keyboard, a mouse, a touchpad, one or more physical buttons, and/or the like. Optionally, the display 138 may be a touch screen display, which includes at least a portion of the user interface 142. For example, a portion of the user interface 142 may correspond to a graphical user interface (GUI) generated by the controller 102, which is shown on the display 138. The touch screen display can detect a presence of a touch from the operator on the display 138 and can also identify a location of the touch with respect to a surface area of the display 138. For example, the user may select one or more user interface icons of the GUI shown on the display by touching or making contact with the display 138. The touch may be applied by, for example, at least one of an individual's hand, glove, stylus, or the like.

The memory 106 includes instructions, parameters, algorithms, models, data values, and/or the like utilized by the controller 102 to perform one or more operations described herein. The memory 106 may be a tangible and non-transitory computer readable medium such as flash memory, RAM, ROM, EEPROM, and/or the like. The memory 106 may include a set of machine learning algorithms 107 (e.g., convolutional neural network algorithms, deep learning algorithms, decision tree learning algorithms, and/or the like) configured to define a plurality of models 109 and an anatomical structure model 108. Additionally or alternatively, the models 109 and/or the anatomical structure model 108 may be received along one of the bi-directional communication links via the communication circuit 104 and stored in the memory 106.

For example, the anatomical structure model 108 may be defined by the machine learning algorithms 107 to identify one or more anatomical structures of interest based on features of the one or more anatomical structures (e.g., boundaries, thickness, and/or the like) within the one or more medical images. The features may represent high level features of the pixels and/or voxels of the medical image such as a histogram orient gradients, blob features, covariance features, binary pattern features, and/or the like. Optionally, the machine learning algorithm 107 may define the anatomical structure model 108 by automatically building a statistical model and/or a database of true positives and true negatives corresponding to each anatomical structure identified based on the features from a set of training images, a classification model, supervised modeling, and/or the like.

For example, the anatomical structure model 108 may be configured and/or designed based on a plurality of training medical images. The plurality of training images may be grouped into different anatomical structure sets, such as organs (e.g., heart, kidney, liver, bladder, lung, brain, and/or the like), skeletal structures (e.g., bone, skull, and/or the like), vascular structures (e.g., artery, vein, and/or the like), regions of a body (e.g., head, torso, and/or the like), and/or the like. Additionally or alternatively, the training images within each set may represent different orientations and/or views of the one or more anatomical structures. For example, a set of the training images may include over 50,000 medical images. For example, a set of the training images may include one or more different views corresponding to the heart. In another example, a second set of the training images may include one or more different views corresponding to the brain.

Additionally or alternatively, the anatomical structure model 108 may be defined based on a supervised learning method. For example, a user (e.g., skilled medical practitioner) may manually label the one or more anatomical structures within the plurality of training medical images utilizing the user interface 142. The manually labeled medical images may be used to build a statistical model and/or a database of true positives and true negatives corresponding to each anatomical structure defining the anatomical structure model 108.

The plurality of models 109 are configured to define a diagnostic procedure for one or more anatomical structures. The diagnostic procedure may represent at least one of identifying a two-dimensional plane, segmenting the anatomical structure of interest, measuring a boundary thickness of the anatomical structure of interest, measuring a volume of the anatomical structure of interest, identifying the anatomical structure within the medical image, annotating objects within the medical image, measuring an area of the anatomical structure of interest, and/or the like. For example, the plurality of models 109 may be defined by the machine learning algorithms 107 corresponding to specific anatomical structures.

For example, at least one of the plurality of models 109 may be defined by the machine learning algorithms 107 to define a two-dimensional plane representing the mid-sagittal plane of a head (e.g., anatomical structure). The at least one model 109 may be configured to identify the mid-sagittal plane of the head defined by the machine learning algorithms 107 utilizing pattern recognition. For example, the controller circuit 102 executing the at least one model 109 is configured to identify structures within the head based on features of the head (e.g., eye socket, internal bone structure, thickness, shape, and/or the like) within the medical image. The features may be based on high level features of the pixels and/or voxels of the medical image such as a histogram orient gradients, blob features, covariance features, binary pattern features, and/or the like. Optionally, the machine learning algorithm 107 may define the at least one model 109 by automatically building a statistical model and/or a database of true positives and true negatives corresponding to each anatomical structure for the at least one model 109 identified based on the features. The controller 102 executing the at least one model 109 may define a two-dimensional plane representing the mid-sagittal plane based on a symmetric plane based on the identified structures.

In another example, at least one of the plurality of models 109 may be defined by the machine learning algorithms 107 to segment a bladder (e.g., anatomical structure) from the medical image. At least one model 109 may be configured to identify the bladder defined by the machine learning algorithms 107 utilizing a classification model (e.g., random forest classifier). The machine learning algorithm 107 defines at least one model 109 based on a pixel level classifier model to label and/or assign each pixel of the medical image into a plurality of categories or classes (e.g., muscle, fat, background anatomy, bladder). The controller 102 executing the classification model may determine the classes from a feature space of the pixels based from the various intensities and spatial positions of pixels within the medical image. The controller 102 executing the at least one model 109 may continually select a pixel of the medical image, and compare characteristics of the select pixel to feature vectors. For example, the controller 102 may compare an intensity or brightness of the select pixel to feature vectors of the classification model. In another example, the controller 102 may determine a variance kurtosis, skewness, or spatial distribution characteristic of the select pixel by comparing the intensity of the select pixel with adjacent and/or proximate pixels around the select pixel.

A number of characteristics of the select pixel compared by the controller 102 may be based on the feature sets included in the feature vectors. Each feature vector may be an n-dimensional vector that includes three or more features of pixels (e.g., mean, variance, kurtosis, skewness, spatial distribution) corresponding to a class (e.g., a background anatomy, muscle tissue, fat, the bladder) of pixels of anatomy within an ultrasound image. The feature vectors of the classification model may be generated and/or defined by the controller based on a plurality of test medical images. For example, the controller 102 may select pixel blocks from one hundred reference ultrasound images. The select pixel blocks may have a length of five pixels and a width of five pixels. For example, a plurality of pixels within each select pixel block may represent and/or correspond to one of the classes, such as tissue of the bladder. Based on the plurality of pixels within the select pixel blocks, the controller 102 may generate and/or define a feature vector. The controller 102 may determine feature sets for each pixel within the plurality of pixels of a select pixel block or more than one select pixel block corresponding to the same class. One of the feature sets may be based on an intensity histogram of the reference ultrasound images. For example, the controller circuit may calculate a mean intensity of the plurality of pixels, a variance of the plurality of pixel intensities, a kurtosis or shape of intensity distribution of the plurality of pixels, a skewness of the plurality of pixels, and/or the like.

Additionally, one of the feature sets may correspond to a position or spatial feature of the pixels within the select pixel block. A spatial position with respect to a position within the reference image (e.g., central location) and a depth with respect to an acquisition depth within the patient. The controller 102 may perform a k-means clustering and/or random forest classification on the feature sets to define feature values that correspond to the class of the select pixel blocks. The controller 102 may define a feature vector corresponding to the class based on the feature values to the classification model. The controller 102 may assign a class to the select pixel based on a corresponding feature vector. When the select pixel is assigned a class, the controller 102 may repeat the classification model to the remaining pixels of the medical image, thereby segmenting the bladder within the medical image.

In this way, the learning algorithms 107, anatomical structure model 108, and models 109 may together form a classification model (also referred to herein as a scan plane and/or anatomical structure detection framework) utilized by the controller 102 to classify stored ultrasound images and/or ultrasound images generated from imaging data (e.g., imaging datasets) acquired in real-time (e.g., during an ultrasound scanning procedure or session). The images and/or image data may be classified by scan plane of an anatomical structure and/or by anatomical landmark/structure such that a target or desired scan plane or anatomical structure is identified by the controller, using the stored models and/or algorithms. The identified target scan plane(s) of an anatomical structure and/or an anatomical structure may then be displayed to a user via the display 138. As discussed further below, position data that corresponds to the acquired imaging data and generated images may be received at the controller 102 and fed into the models and/or algorithms in memory 106 to enhance and/or check the classification models and outputs. As also discussed further below, the corresponding position data and imaging data (or images) may be inputs into the models 109, anatomical structure model 108, and/or learning algorithms 107.

It may be noted that the machine learning algorithms utilized to define the plurality of models 109 and/or the anatomical structure model 108 are examples, additional methods are available for a person of ordinary skill in the art.

Turning to FIG. 1B, the MDS 150 may be integrated with and/or a part of a medical diagnostic imaging system. For example, the MDS 150 includes an ultrasound imaging system. The MDS 150 includes an ultrasound probe 126 having a transmitter 122, transmit beamformer 121, probe/SAP electronics 110, and a position sensor 112. The probe/SAP electronics 110 may be used to control the switching of the transducer elements 124. The probe/SAP electronics 110 may also be used to group transducer elements 124 into one or more sub-apertures.

The ultrasound probe 126 may be configured to acquire ultrasound data or information from the anatomical structures (e.g., organ, blood vessel, heart) of the patient based on the predetermined settings. Additionally, the ultrasound probe 126 may acquire position information (e.g., data), via the position sensor 112, that includes the spatial position, relative to a coordinate system and a reference point which may be predefined by the controller, of the probe 126. The position data may correspond to the acquired ultrasound image data, such that each image (or scanned image plane or frame) includes a corresponding position of the probe at the time the image data was acquired. The ultrasound probe 126 is communicatively coupled to the controller 102 via the transmitter 122. The transmitter 122 transmits a signal to a transmit beamformer 121 based on acquisition settings received by the controller 102. The acquisition settings may define an amplitude, pulse width, frequency, gain setting, scan angle, power, time gain compensation (TGC), resolution, and/or the like of the ultrasonic pulses emitted by the transducer elements 124. The probe 126 may include an additional transmitter for transmitting the signals formed by the transmit beamformer 121. The transducer elements 124 emit pulsed ultrasonic signals into a patient (e.g., a body). The acquisition settings may be defined by the user utilizing the user interface 142. The signal transmitted by the transmitter 122 in turn drives a plurality of transducer elements 124 within a transducer array 112.

The transducer elements 124 emit pulsed ultrasonic signals into a body (e.g., patient) or volume corresponding to the acquisition settings along one or more scan planes. The ultrasonic signals may include, for example, one or more reference pulses, one or more pushing pulses (e.g., shear-waves), and/or one or more pulsed wave Doppler pulses. At least a portion of the pulsed ultrasonic signals back-scatter from the anatomical structures (e.g., heart, left ventricular outflow tract, breast tissues, liver tissues, cardiac tissues, prostate tissues, neonatal brain, embryo, abdomen, and the like) to produce echoes. The echoes are delayed in time and/or frequency according to a depth or movement, and are received by the transducer elements 124 within the transducer array of the probe 126. The ultrasonic signals may be used for imaging, for generating and/or tracking shear-waves, for measuring changes in position or velocity within the anatomic structure, differences in compression displacement of the tissue (e.g., strain), and/or for therapy, among other uses. For example, the probe 126 may deliver low energy pulses during imaging and tracking, medium to high energy pulses to generate shear-waves, and high energy pulses during therapy.

The transducer elements 124 convert the received echo signals into electrical signals which may be received by a receiver 128. The receiver 128 may include one or more amplifiers, an analog to digital converter (ADC), and/or the like. The receiver 128 may be configured to amplify the received echo signals after proper gain compensation and convert these received analog signals from each transducer element 124 to digitized signals sampled uniformly in time. The digitized signals representing the received echoes are stored in memory 106, temporarily. The digitized signals correspond to the backscattered waves receives by each transducer element 124 at various times. After digitization, the signals still may preserve the amplitude, frequency, phase information of the backscatter waves. The receiver 128 may also transmit positional data, received from the position sensor 112 to the controller 102 and/or memory 106.

Optionally, the controller 102 may retrieve the digitized signals stored in the memory 106 to prepare for the beamformer processor 130. For example, the controller 102 may convert the digitized signals to baseband signals or compressing the digitized signals.

The beamformer processor 130 may include one or more processors. Optionally, the beamformer processor 130 may include a central controller circuit (CPU), one or more microprocessors, or any other electronic component capable of processing inputted data according to specific logical instructions. Additionally or alternatively, the beamformer processor 130 may execute instructions stored on a tangible and non-transitory computer readable medium (e.g., the memory 106) for beamforming calculations using any suitable beamforming method such as adaptive beamforming, synthetic transmit focus, aberration correction, synthetic aperture, clutter reduction and/or adaptive noise control, and/or the like. Optionally, the beamformer processor 130 may be integrated with and/or apart of the controller. For example, the operations described being performed by the beamformer processor 130 may be configured to be performed by the controller 102.

The beamformer processor 130 performs beamforming on the digitized signals of transducer elements and outputs a radio frequency (RF) signal. The RF signal is then provided to an RF processor 132 that processes the RF signal. The RF processor 132 may include one or more processors. Optionally, the RF processor 132 may include a central controller circuit (CPU), one or more microprocessors, or any other electronic component capable of processing inputted data according to specific logical instructions. Additionally or alternatively, the RF processor 132 may execute instructions stored on a tangible and non-transitory computer readable medium (e.g., the memory 106). Optionally, the RF processor 132 may be integrated with and/or apart of the controller 102. For example, the operations described being performed by the RF processor 132 may be configured to be performed by the controller 102.

The RF processor 132 may generate different ultrasound image data types, e.g. B-mode, color Doppler (velocity/power/variance), tissue Doppler (velocity), and Doppler energy, for multiple scan planes or different scanning patterns based on the predetermined settings of the first model. For example, the RF processor 132 may generate tissue Doppler data for multi-scan planes. The RF processor 132 gathers the information (e.g. I/Q, B-mode, color Doppler, tissue Doppler, and Doppler energy information) related to multiple data slices and stores the data information, which may include time stamp and orientation/rotation information, in the memory 106.

Alternatively, the RF processor 132 may include a complex demodulator (not shown) that demodulates the RF signal to form IQ data pairs representative of the echo signals. The RF or IQ signal data may then be provided directly to the memory 106 for storage (e.g., temporary storage). Optionally, the output of the beamformer processor 130 may be passed directly to the controller 102.

The controller 102 may be configured to adjust the system settings, image presentation settings, and/or anatomical structures represented by the ultrasound data and/or ultrasound images acquired by the MDS 150. For example, the controller 102 may be configured to process the acquired ultrasound data (e.g., RF signal data or IQ data pairs) and prepare and/or generate frames of ultrasound image data representing the anatomical structure for display on the display 138. Acquired ultrasound data may be processed in real-time by the controller 102 during a scanning or therapy session as the echo signals are received. Additionally or alternatively, the ultrasound data may be stored temporarily in the memory 106 during a scanning session and processed in less than real-time in a live or off-line operation.

For the purposes of this disclosure, the term "real-time" is defined to include a procedure that is performed without any intentional delay. For example, an embodiment may acquire images at a real-time rate of 7-20 frames/sec. The ultrasound imaging system 100 may acquire 2D data of one or more planes at a significantly faster rate. However, it should be understood that the real-time frame-rate may be dependent on the length of time that it takes to acquire each frame of data for display. Accordingly, when acquiring a relatively large amount of data, the real-time frame-rate may be slower. Thus, some embodiments may have real-time frame-rates that are considerably faster than 20 frames/sec while other embodiments may have real-time frame-rates slower than 7 frames/sec. The data may be stored temporarily in a buffer (not shown) during a scanning session and processed in less than real-time in a live or off-line operation.

The memory 106 may be used for storing processed frames of acquired ultrasound data that are not scheduled to be displayed immediately or to store post-processed images (e.g., shear-wave images, strain images), firmware or software corresponding to, for example, a graphical user interface, one or more default image display settings, programmed instructions, and/or the like. The memory 106 may store 2D and/or 3D ultrasound image data sets of the ultrasound data, where such 2D and/or 3D ultrasound image data sets are accessed to present 2D and 3D images. For example, a 2D or 3D ultrasound image data set may be mapped into the corresponding memory 106, as well as one or more reference planes. The processing of the ultrasound data, including the ultrasound image data sets, may be based in part on user inputs, for example, user selections received at the user interface 142.

The ultrasound imaging system of MDS 150 may continuously acquire data at a frame-rate of, for example, 10 Hz to 30 Hz (e.g., 10 to 30 frames per second). Images generated from the data may be refreshed at a similar frame-rate on display device 118. Other embodiments may acquire and display data at different rates. For example, some embodiments may acquire data at a frame-rate of less than 10 Hz or greater than 30 Hz depending on the size of the frame and the intended application. A memory 120 is included for storing processed frames of acquired data. In an exemplary embodiment, the memory 106 is of sufficient capacity to store at least several seconds worth of frames of ultrasound data. The frames of data are stored in a manner to facilitate retrieval thereof according to its order or time of acquisition. The memory 106 may comprise any known data storage medium.

In various embodiments of the present invention, one or more components of MDS 150 may be included in a portable, handheld ultrasound imaging device. For example, display 138 and user interface 142 may be integrated into an exterior surface of the handheld ultrasound imaging device, which may further contain controller 102, beamformer processor 130, RF processor 132, and memory 106. Probe 106 may comprise a handheld probe in electronic communication with the handheld ultrasound imaging device to collect raw ultrasound data. Transmit beamformer 121, transmitter 122, and receiver 128 may be included in the same or different portions of the ultrasound imaging system 100. For example, transmit beamformer 121, transmitter 122, and receiver 128 may be included in the handheld ultrasound imaging device, the probe, and combinations thereof.

Turning now to FIGS. 2A-2B, a flow chart of a method 200 for classifying diagnostic medical images and guiding a user of an imaging system, during an imaging procedure, based on image data and position data of the medical imaging probe is shown. Method 200 may be implemented with a medical diagnostic system (MDS), such as the MDS 100 and/or 150 shown in FIGS. 1A and 1B, respectively. In one embodiment, the MDS includes an ultrasound imaging system, such as the ultrasound imaging system shown in FIG. 1B. Instructions for carrying out method 200 may be executed by a controller or processor of the MDS (e.g., controller 102) based on instructions stored on a memory of the controller or processor and in conjunction with signals received from sensors of the imaging system (such as echoes received by the receiver, probe position data received by the receiver, and signals received from the user interface described above with reference to FIGS. 1A-1B). In one embodiment, the controller may include multiple controllers and/or processors and memory, such as one or more of controller 102, beamformer processor 130, memory 106, and RF processor 132 shown in FIG. 1B. The controller or processor may employ actuators (such as the transmitter, transmit beamformer, display, and probe) of the imaging system to adjust imaging system operation, according to the methods described below.

Method 200 starts at 202 by determining operating conditions of the MDS and receiving user inputs. Receiving user inputs may include receiving inputs from a user interface (e.g., user interface 142 shown in FIGS. 1A-1B) that are input by a user, such as a medical technician, physician, or other medical professional User inputs may include a gestational age of a patient, a fetal position, a fetal weight, breech/cephalic position information, a target organ or anatomical landmark/structure (such as fetus, fetal head, fetal heart, liver, kidney, or the like), a target scan plane (such as axial, coronal, transverse, and the like), a desired scan protocol, and the like. In some embodiments, the method at 202 may include prompting the user, via the display of the MDS (e.g., display 138), to input one or more user inputs based on initial inputs received at the controller from the user interface. For example, if a certain scan protocol (including a region of a patient's body to be imaged, as one example, or a particular type of ultrasound exam, such as a fetal ultrasound) is selected or a target organ and/or scan plane is input, the controller may send additional prompts for user inputs to the display, such as gestational age, fetal position, and/or fetal weight if the selected imaging procedure is a fetal ultrasound.

The method proceeds to 204 to determine whether the user, via the probe (e.g., probe 126 shown in FIG. 1B), has navigated to a target organ or anatomical structure (e.g., the desired organ or anatomical feature to be imaged for medical diagnosis). For example, some imaging scan protocols may start from a specific anatomical structure or organ. In other examples, other imaging scan protocols may start from a same, predetermined reference position. In yet another example, a user may be able to navigate the probe to a target organ, but then has trouble finding a particular scan plane within the target organ that contains the desired view (e.g., for the scan protocol or desired imaging procedure). In still another example, a user may require help in navigating to a target organ to begin the imaging procedure or scan protocol. The method at 204 may include determining that the user has navigated to a target organ or anatomical structure based on feedback from one or more image recognition models stored in memory of the controller (such as anatomical structure model 108 and/or models 109 shown in FIG. 1A). For example, image data acquired with the imaging probe, at the current location on the patient may be sent to the controller to form one or more images and the one or more images are then analyzed by one or more image recognition algorithms or models stored at the controller. The output of the algorithms and/or models may be an indication of whether the target organ or anatomical structure for the desired imaging procedure or scan protocol has been imaged by the probe. In another example, the controller may determine that the user has navigated to the target organ or anatomical structure based on a received user input confirming the probe is at the target organ or anatomical structure. In this example, the controller may confirm the probe is imaging the target organ or anatomical structure based on feedback from the one or more stored image recognition models.

If the method determines that the user has not navigated to the target organ or anatomical structure, the method proceeds to 206 to prompt the user via the display to navigate the probe to a predetermined reference position. For example, a predetermined reference position for the imaging procedure may be stored in the memory of the controller and an alert or prompt may be displayed via the display, asking the user to navigate to the predetermined reference position. As one example, during a fetal ultrasound procedure, the predetermined reference position may be the BPD plane in the fetal head (e.g., plane for biparietal diameter, which is the widest transverse diameter of the fetal head, which may be an axial scan plane through the fetal head). The predetermined reference position may be a relatively easy position and/or scan plane to find, even by a more inexperienced user. In some embodiments, the method at 206 may additionally include providing direction or guidance on how to move the probe to the predetermined reference position and/or anatomical structures to look for in the predetermined reference position. This guidance and/or direction may be displayed to the user via the display in the form of a dialog box or pop-up screen, in one example.

Alternatively at 204, if the user has navigated to the target organ or anatomical structure, the method proceeds to 208 to determine the desired reference position for the target organ or anatomical structure and then prompt the user to navigate to the determined reference position. For example, a predetermined reference position for each target organ or anatomical structure, or for a particular imaging procedure or scan protocol, may be stored in the memory of the controller (e.g., in the form of a look-up table). In this way, different target organs may have different, predetermined and stored reference positions that may be looked up during an imaging procedure, while the user is scanning the patient. The controller may then send a signal to the display to display, via a pop-up window or dialog box, as an example, instructions to the user to navigate to the determined reference position for the target organ. As one example, during a fetal ultrasound procedure, the determined reference position for the probe may be the transventricular (TV) plane in the fetal head. In some embodiments, the method at 208 may additionally include direction or guidance on how to move the probe to the determined reference position and/or anatomical landmarks to look for in the determined reference position. This guidance and/or direction may be displayed to the user via the display in the form of a dialog box or pop-up screen, in one example.

At 210, the method includes receiving confirmation that the user has positioned the probe at the reference position, acquiring image data and position information from the probe, at the reference position, and calibrating the position sensor of the probe. In one example, the method at 210 may include receiving an input from the user (e.g., via the user interface) that the probe has been positioned at the desired reference position (e.g., the predetermined reference position requested and indicated to the user by the controller). Additionally or alternatively, the method may include confirming the probe is at the reference position by acquiring image data and position information from the probe (e.g., via the transducer elements and the position sensor on the probe, respectively) and analyzing the acquired image data, at one or more image analysis models or frameworks (as discussed above with reference to the models stored in memory 106 in FIG. 1A). For example, the image data and/or images generated from the acquired image data, when the probe is positioned at the desired reference position, may be fed into one or more anatomical structure models, image recognition models, scan plane detection frameworks (e.g., algorithms), and the like. These models, frameworks, and/or algorithms, stored in the memory of the controller, may compare the acquired image or image data against stored images or image data and determine whether the acquired image matches anatomical landmarks/features of stored images at the reference position. If the controller determines, based on these models and/or algorithms that the ultrasound probe is at the desired reference position, the controller may store the corresponding image data (and/or generated image) and position data from the probe at the reference position. This position may then be stored as an origin of a coordinate system and all other positions of the probe (e.g., position data output by the position sensor on the probe) may be determined relative to this origin. In some embodiments, the reference position may additionally be determined/confirmed based on a-priori information, such as one or more inputs from the user received at 202. For example, the reference position may be determined based on an output of the probe, image data acquired at the reference position, and one or more user inputs. In this way, the position sensor of the probe, and the positional output of the sensor, is calibrated based on the predetermined reference position and image data acquired at that location and, in some embodiments, user inputs. The reference position described above is used as a landmark for calibrating the algorithms, models, and frameworks described herein. In some embodiments, additional landmark positions may be beneficial and provide additional information for increasing the accuracy of the models/algorithms/frameworks. For example, at 208, the method may include prompting the user to navigate to several reference positions and acquire and store image data at each of the reference positions (e.g., the fetal heat, feet, and abdomen). The head position may be used as the initial reference position (origin) and then, together with the input cephalic/breech information, an anatomic model relative to the reference position and these landmarks may be calibrated. This model then describes how the fetus is spatially oriented, which will help in indicating to the user where to move the probe next.

The method proceeds to 211 to initialize the algorithms and models according to a selected scan protocol. A scan protocol may include a list of the images and measurements that should be acquired during a specified ultrasound examination (e.g., procedure). The list of images may include specified scan planes at certain organs or anatomical landmarks. For example, the list may include a particular plane (e.g., scan plane) within the organ or anatomical feature that contains the desired view. Each protocol may include a plurality of these desired views or images and corresponding measurements to be taken. Each item in the scan protocol may utilize individual models and algorithms (e.g., first item head, second item heart). Thus, before starting a scan protocol item, the method at 211 may include selecting the appropriate models and algorithms (e.g., the models and algorithms that correspond to the anatomical part to be scanned in the scan protocol item) for the next scan protocol item.

At 212, the method includes determining whether guidance is being used or requested (by the user) for the current imaging procedure and scan protocol. As explained above, more inexperienced users may have difficulties finding the target planes for the desired views. Thus, as described further below, the scan plane detection framework, using the acquired position sensor data and corresponding image data as inputs, may aid the user in finding the correct planes and/or automatically select the desired planes and/or views for the set scan protocol from a plurality of images taken by the user. The controller may determine that a set scan protocol is being used based on one or more user inputs received at the controller from the user interface (such as selection of a set scan protocol from a menu, an input, via a keyboard, of the desired scan protocol, and/or the selection of a specific ultrasound procedure which may have a corresponding set scan protocol stored in the memory of the MDS and/or controller).

If the method determines that guidance is being used or requested, the method continues to 214 to indicate to the user, via the display, where to move the probe on the patient. For example, the method at 214 may include determining the next desired view and scan plane in the set scan protocol and the position of the next desired view and scan plan relative to the calibrated reference position. Assuming the probe is at the reference position, the controller may determine coordinates of, a direction to, a distance to, and/or anatomical landmarks at the next desired view and scan plane and relay these directions, coordinates, and/or landmarks to the user via the display (e.g., via a dialog box, pop-up menu, or the like). As one example, the directions displayed to the user on how/where to move the probe may include up/down/left/right, relative to the current probe position, and/or toward a patient's head/right arm/left arm/feet and/or rotate the probe clockwise or counterclockwise by X degrees. In yet another example, the directions may additionally include an approximate distance to move the probe (such as 3 inches toward the patient's head). As another example, the method at 214 may include displaying an anatomical model of the baby (e.g., patient), highlighting the current scan plane/location and the target scan plane/location of the probe on the displayed anatomical model, and updating the display of the highlighting while a user is moving the probe and scanning. In this embodiment, the user can see whether he/she is moving towards the target location or away from it. In yet another embodiment, the method at 214 may additionally or alternatively include displaying the distance towards the target scan plane/location graphically (e.g., current position as a slider on a distance bar. Thus, the method at 214 may include, outputting to the display text and/or visual instructions on how and/or where to move the probe relative to the probe's current position. After guiding the user where to move the probe, via the displayed indication, and/or if guidance is not being used, the method continues to 216.

At 216, the method includes continuously monitoring received image data and position data (received from the probe) during the imaging procedure, while the user moves the probe across or within the patient. For example, the method at 216 may include acquiring, via the transducer elements of the probe, image data and generating images from the acquired image data. At 216, the method may additionally include displaying the generated images (via the display) to the user, in real-time, as they are acquired. The image data may include 2D or 3D image data. The method at 216 also includes acquiring position data, from the position sensor on the probe, at the same time as acquiring the image data. The position data corresponds to the acquired image data. For example, at any given time and location of the probe, a set of image data and position data are acquired and linked to one another. At 214, the method includes inputting the acquired and linked image data (and/or generated images from the image data) and position data into a scan plane and/or anatomical structure detection framework. This may include, at 218, identifying an anatomical structure and/or detecting a scan plane using the detection framework and the input image data. The method at 214 may further include comparing the identified anatomical structures and/or scan planes with the corresponding, input position data.

FIG. 3 shows an example block diagram of the scan plane and/or anatomical structure detection framework 302. The detection framework 302 may be an artificial intelligence and machine learning framework that includes one or more algorithms and models, such as one or more of the learning algorithm 107, anatomical structure model 108, and models 109 discussed above with reference to FIG. 1A. The one or more algorithms and models of the detection framework 302 are stored in the memory (e.g., memory 106) of the MDS, which may be included within or operably coupled to the controller and may include a classification model/framework which classifies the received image data and/or generated images into certain scan planes and/or image views according to stored data and the algorithms and/or models. For example, as shown in FIG. 3, the inputs 304 to the detection framework 302 may include the acquired position data and image data. Since image data and position data are continuously being acquired during an imaging procedure, the inputs 304 may be continuously fed into the detection framework 302. The detection framework 302 then classifies the acquired images as a particular scan plane or view of a certain anatomical structure (e.g., TV plane in fetal head). At the same time, the detection framework 302 may determine a location of the acquired image, which may include a scan plane and/or anatomical structure, based on the input position data. The detection framework 302 may then compare the classified scan plane from the acquired image to the determined location from the acquired position data to see whether the classified planes and locations match. For example, the detection framework 302 may determine whether the position sensor data and image data both indicate the probe being at the same location and scan plane or whether there is a mismatch between the two inputs (e.g., the position data suggests the probe cannot be at the scan plane/anatomical structure indicated by the classified image). Thus, the outputs 306 of the detection framework may include one or more of a mismatch warning (e.g., the scan plane or location detected from the image data does not match the scan plane or location detected from the corresponding position data), guidance on where/how to move probe (e.g., guidance or directions on where to move the probe to obtain the required view or scan plane and how to get to the next view or scan plane in the set protocol), and/or an indication that the target scan plan and/or anatomical structure was imaged and a display of the target scan plane and/or anatomical structure. These warnings, guidance/directions, and/or target scan planes or views may all be displayed to the user via the display of the MDS, via an image, pop-up dialog box, indicator light, or the like. Additionally or alternatively, the identified target scan plane and resulting image displayed to the user (one of outputs 306) may be based on both the image data and position data. For example, the position data may be used within the scan plane detection framework 302 to update or modify the resulting scan plane detected in the framework 302 from the image data alone. In this way, the position data may be used to correct or update the final scan plane detected via the scan plane detection framework 302. Thus, the position data may enhance and increase the accuracy of the scan plane classification and identification output at 306.

Returning to FIG. 2A, method 200 continues to 222 to determine whether there is a mismatch between planes classified and detected based on the image and position data, as explained above with reference to FIG. 3. For example, if the plane detection framework (e.g., scan plane detection framework 302 shown in FIG. 3) identifies different scan planes and/or target organs based on the input image data and input position data, then there may be a mismatch between these two data sources. In another example, the detection framework may determine there is a mismatch between the image data and position data if the framework identifies a first anatomical structure based on the input image data and a second position based on the input position data, where it is not physically possible (based on anatomy) for the probe to image the first anatomical structure at the second position. In this way, even if the target scan plan has not yet been identified (since it has not been found and imaged by the user yet), the detection framework may still continuously detect whether the position data and image data correspond one another or whether there is a mismatch between the detected anatomical structures and locations of the image and position data streams. In still another example, the system may determine there is a mismatch if the detected planes or anatomical structures using the image data and position data mismatch by greater than a threshold percentage (such as 40%, 50%, or the like). In this way, a mismatch that results in recalibration (as described further below with reference to 224) may only be indicated if the detected plane (or anatomical structure) based on the image data differs from the detected plane (or anatomical feature) based on the position by more than the threshold percentage.

At 222, if it is determined that there is a mismatch between the detected scan planes or detected anatomical structure and the location of that anatomical feature for the image data and position data, the method continues to 224 to direct the user to recalibrate the probe position. Said another way, if the framework determines, based on the image data and position data, that it is not possible for the detected plane or anatomical structure to be in the position indicated by the position sensor data, the system determines there is a mismatch between the data sources and the method continues to 224. The method at 224 may include sending an alert to the display of the MDS and displaying the alert which indicates to the user that they should navigate the probe to the predetermined and indicated reference position and acquire imaging data at that reference position. The predetermined reference position may be determined as explained above with reference to the methods at 206 and/or 208. The alerts may include an indicator light on the display, a pop-up dialog box, and/or text on a screen of the display. The method then returns to 210 to calibrate the position of the probe.

Returning to 222, if there is no mismatch between the detected scan planes for the image data and position data, the method continues to 226, as shown in FIG. 2B, to determine whether the target scan plane of the anatomical structure has been identified by the detection framework. For example, for the current scan protocol, the user may be trying to find a specific scan plane of an anatomical structure. As explained above with reference to FIG. 3, the detection framework may determine that the target scan plane has been found based on the image data and position data input into the models and/or algorithms of the framework. A continuous stream of image and position data may be fed into the detection framework, and once the framework identifies the target scan plane and/or anatomical structure within the acquired image(s) (generated from the image data), the framework may output an indication that the target plane has been identified and display the corresponding image (generated from the image data) via the display, as shown by the method at 228. The method at 228 may additionally include asking the user for confirmation of the identified target plane of the anatomical structure. For example, the method at 228 may include displaying the identified image of the target plane, structure, and/or organ and then prompting the user, via a dialog box, pop-up menu, and/or text on the display to confirm that the image is the desired view including the target scan plane of the anatomical structure.

If the controller, via the detection framework, determines that the target scan plane or anatomical structure has not (yet) been found, the method proceeds to 227 and includes providing the user guidance on how/where to move the probe to obtain the desired view, including the target scan plane of the anatomical structure (similar to as described above with reference to the method at 214). For example, based on the scan plane or anatomical structure detected by the detection framework, based on the image data and position data, the controller may determine in what direction (e.g., toward a patient's head, left arm, legs, or the like) and how far (e.g., 2 inches, 3 inches, 1 mm, or the like) to move the probe from its current position (e.g., the current position at which the analyzed image data and position data were acquired). The method may include displaying these directions to the user via the display. The method may then return to 216 to continue to continuously receive image data and position data from the probe, as a user moves the location of the probe on/in the patient. In this way, imaging data and corresponding position data is continuously acquired and analyzed by the detection framework, and guidance to the user on how to move the probe may continue to be provided, until the target scan plane of the desired anatomical structure is identified. While this continuous monitoring is occurring, the images generated from the imaging data are continuously displayed to the user via the display.

From the method at 228, the method continues to 230 to determine whether the displayed image was confirmed as showing the target scan plane of the anatomical structure. As one example, the controller may receive a user input signal, via the user interface, indicating whether the user confirms or rejects the displayed image. If the controller receives a signal indication that the user does not confirm or rejects the image, the method proceeds to 232 to update the detection framework and then proceeds to 227 to provide guidance on how/where to move the probe and then return to the method at 216 in FIG. 2A, as described above. Updating the detection framework may include using the identified image to update the machine learning algorithms 107, anatomical structure models 108, and/or models 109, as described above with reference to FIG. 1A. In this way, the detection framework may learn what the target scan plane or anatomical feature looks like based on the originally identified image not being the correct one. In this way, the algorithms and/or models of the detection framework may be continuously updated in order to increase the detection accuracy and outputs of the framework.

Alternatively at 230, if the identified image is confirmed, the method continues to 234 to store the identified image and set the scan protocol to the next target plane. Storing the image may include storing the classified image (e.g., including the name of the target plane and/or anatomical structure) and any associated measurements taken for that image. The controller may then set the next target scan plane in the scan protocol and return to the method at 211 in FIG. 2A, as described above. In this way, method 200 may repeat until the set scan protocol is complete and/or until a user indicates the imaging procedure is finished (e.g., via a user input at the user interface).

Optionally, method 200 may continue from 234 to 236 before returning to 211. At 236, the method includes invoking an additional organ-specific model within the detection framework. For example, the detection framework (detection framework 302 shown in FIG. 3) may include one or more anatomical structure specific image and/or scan plane detection models configured to identify scan planes and/or anatomical structures in a specific anatomical structure (e.g., for fetal heart detection). The anatomical structure may be an organ (e.g., heart, kidney, bladder, lung, brain, and/or the like), skeletal structure (e.g., bone, skull, and/or the like), vascular structure (e.g., artery, vein, and/or the like), region of body (e.g., head, torso, and/or the like), and/or the like. The detection framework may identify the anatomical structure, for example, utilizing one or more machine learning algorithms and models (such as the algorithms and models discussed above). Then, based on the identified anatomical structure (which may be a specific organ), one or more of a plurality of models representing specialized diagnostic procedures are manually and/or automatically selected for subsequent analysis of the anatomical structure within the acquired medical image. For example, the plurality of models may be the models 109 shown in FIG. 1A, as described above. The plurality of models may be grouped according to the anatomical structure corresponding to the diagnostic procedure executed by the plurality of models. Based on an identified anatomical structure of the image, as identified by the anatomical structure model 108 shown in FIG. 1A, in one example, the controller may select a corresponding anatomical structure model (e.g., one of the plurality of models). The controller may then perform a diagnostic procedure for the identified anatomical structure, which may include calculating dimensions of a structure in the image, classifying (e.g., identifying) additional features within the image (e.g., such as identifying the right ventricle when the anatomical structure is the heart), identifying a boundary of one or more of the additional features, and the like. In this way, further classification and processing of the generated image may be performed according to an anatomical structure (e.g., organ) specific model stored in the memory of the controller (or operably coupled to the controller). As explained further below, the method at 236 may be performed online (e.g., during an imaging procedure while a user is actively moving the probe on the patient and acquiring image data) or offline (after the conclusion of the imaging procedure, on stored images and position data).

In one embodiment, method 200 is performed during an imaging procedure, while a user is actively scanning the patient with the probe (e.g., online mode). In another embodiment, a portion of method 200 may be performed after an imaging procedure, after a set of imaging data (e.g., images) and corresponding probe position data has been acquired and stored in a memory of the MDS. In this embodiment, method 200 includes retrieving the stored images and position data at 202, performing the method at 216 with the stored images and position data, and continuing to perform the method at 226 where the method may include continuing to analyze the stored images and position data via the detection framework until the target planes and/or anatomical structures are found. The method may then proceed to 228 which may include displaying the identified target plane(s) or anatomical structures/landmarks to the user via the display and/or saving the identified target plane(s) and/or anatomical structures/landmarks for a user (such as a radiologist) to review (at a later time) and use to make a medical diagnosis.

The medical diagnostic system (MDS) described above with reference to FIGS. 1A-1B may be configured to performed the operations described herein with reference to FIGS. 2A-2B and 3, during a scan and/or offline (e.g., after scanning utilizing stored one or more medical images).

FIGS. 4A-4D show examples of different prompts displayed to a user of an ultrasound imaging system during an imaging procedure, according to the guiding and image classification method described above with reference to FIGS. 2A-2B. Specifically, FIGS. 4A-4D each show an ultrasound imaging system 400, which may be included in one of the MDS shown in FIGS. 1A-1B. The ultrasound imaging system includes a display 402 (similar to display 138 shown in FIG. 1B), imaging probe 404 (similar to probe 126 shown in FIG. 1B), a patient 406, and user (e.g., ultrasound technician) 408. As the user 408 moves the probe 404 across a body of the patient 406, image data and position data are acquired from the probe and an image 410 generated from the acquired image data is continuously displayed on a screen of the display 402.

As shown at FIG. 4A, at a beginning of the imaging procedure, the user may already have navigated to fetal head. However, the scan plane displayed via the image 410 in FIG. 4A may not be the correct plane for obtaining the reference position of the position sensor. Thus, the display 402 may display a dialog box 412, while still displaying the image 410, which prompts the user to navigate to the TV plane in the fetal head for probe calibration, as discussed above with reference to 208 in FIG. 2A. The user may then move the probe to the desired reference position, as shown in FIG. 4B. The displayed image is now at the TV plane in the fetal head. In FIG. 4B, the dialog box 412 asks the user if they are at the reference position (TV plane in fetal head) and asks the user to enter yes (Y) or no (N). The user may then use a user interface of the ultrasound imaging system 400 (e.g., a keyboard) to enter "Y", indicating the probe is at the desired reference position. The system may then calibrate the position of the probe, as discussed above with reference to 210 in FIG. 2A.

Figure 4C:
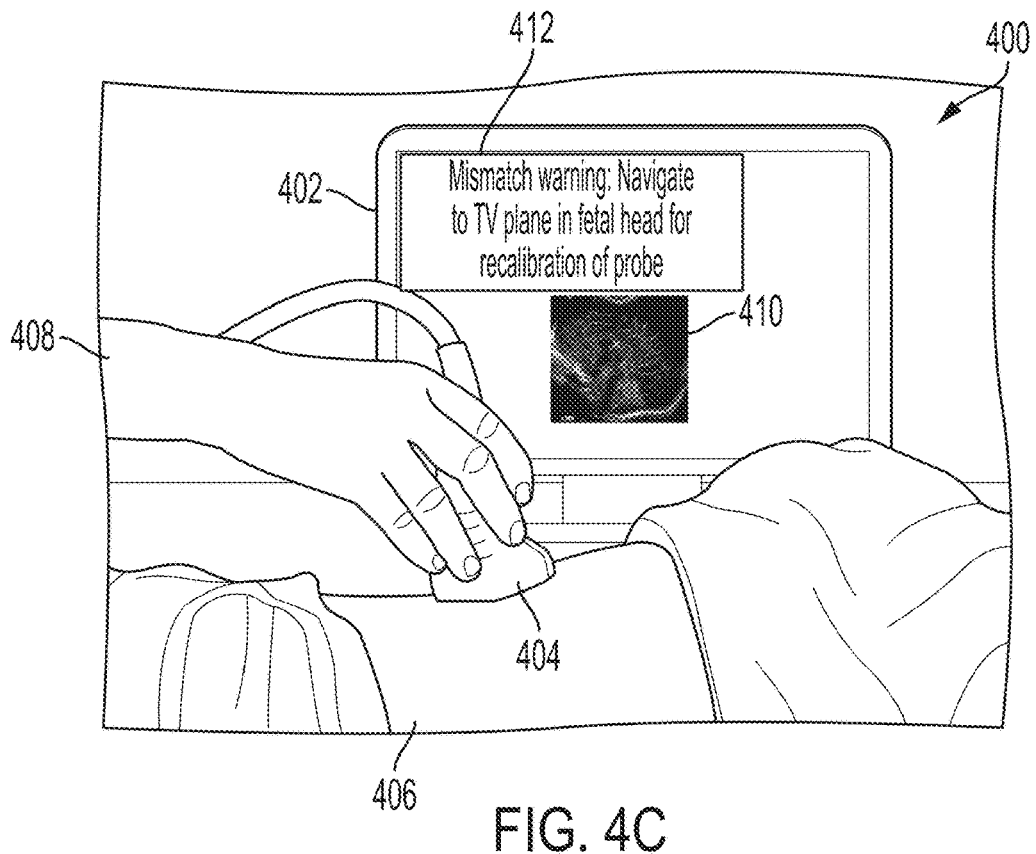

At FIG. 4C, the user may be continuing to move the probe and acquire image and position data. The detection framework, as discussed above with reference to FIGS. 2A-2B and FIG. 3 may determine from the acquired image data and position data that the displayed image 410 is of the mid-sagittal plane in the fetal head, while the position data indicates that the probe should be imaging the trans-cerebellar plane. Thus, there may be a mismatch between the position data and image data. Thus, as discussed above with reference to 222 and 224 in FIG. 2A, the dialog box 412 of the display 402 prompts the user to navigate the probe to the reference position (TV plane) and acquire imaging data at that reference position in order to recalibrate the position sensor of the probe.

Figure 4D:
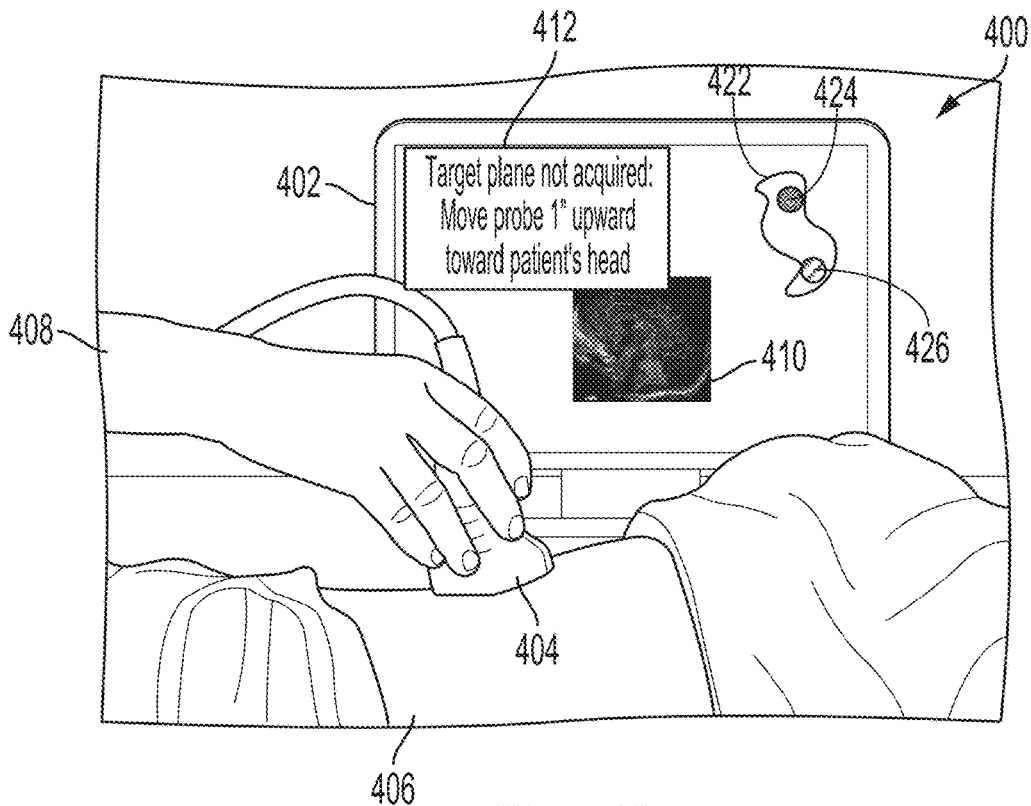

At FIG. 4D, the system may determine that the target plane has not been found (similar to as described above with reference to 226 and 227 in FIG. 2B). For example, as shown in FIG. 4D, the user may be imaging the mid-sagittal plane in the fetal head, as shown by displayed image 410, but the target plane may be the trans-thalamic plane in the fetal head. Thus, as describe above at 227 in FIG. 2B, the system may display, at the dialog box 412, guidance on how the user should move the probe to acquire the target scan plane of the fetal head. For example, as shown in FIG. 4D, the dialog box 412 reads, "target plane not acquired: move probe 1" upward toward patient's head". In some embodiments, as shown in FIG. 4D, providing guidance to the user on how to move the probe may additionally or alternatively include displaying an anatomical model of the baby (e.g., patient) 422, highlighting the current scan plane/location (as shown at circle 424) and the target scan plane/location (as shown at circle 426) of the probe on the displayed anatomical model, and updating the display of the highlighting while a user is moving the probe and scanning (as described above with reference to the method at 214). The anatomical model 422 may be a visual representation of the baby/patient, and may also be specific to the patient, as defined by the anatomical models/algorithms and reference point data taken at the beginning of the imaging procedure. The user may then move the probe as directed by the dialog box 412, or as directed by anatomical model 422. It should be noted that the example instructions given in the dialog boxes 412 of FIGS. 4A-4D are exemplary in nature and other prompts and directions are possible, depending on the imaging procedure and specific patient situation.

In this way, position sensor data from a position sensor on a medical imaging probe (such as an ultrasound transducer probe) is acquired, along with image data, and used to classify images generated from the image data and provide guidance to a user operating the probe during an imaging procedure. The position sensor data and image data may be acquired at the same time, during an imaging procedure, and each image generated from the acquired image data may have corresponding position data (e.g., a coordinate, location relative to a reference point, and/or anatomical structure at the location). The position data and image data or generated images may be fed into a scan plane and/or anatomical structure detection framework made up of one or more machine learning algorithms, anatomical structure models, and anatomical structure specific diagnostic models stored in a memory of a controller. The position data and corresponding images are inputs into the detection framework and outputs of the framework may include mismatch warnings displayed to a user, guidance on where/how to move the probe to obtain the target scan plane of the anatomical structure and/or view, and/or classification and selection of the target scan plane of the anatomical structure and displaying the target scan plane of the structure to the user. During the online mode, the method described above with reference to FIGS. 2A-2B and 3 may provide real-time guidance and feedback to a user, enabling them to more easily find and obtain target scan planes for a scan protocol and/or target anatomical features. This may enable a healthcare provider reviewing the resulting images to make a more accurate medical diagnosis. Additionally, in either an online or offline mode, the position sensor data may increase the accuracy of the detection framework, thereby allowing the images with the target scan planes and/or anatomical features to be identified with increased accuracy and increasing an accuracy of a resulting medical diagnosis based on the detected images.

The technical effect of outputting to a user, instructions for navigating a medical imaging probe from a current scan position to a next scan position for obtaining a desired scan plane of a target anatomical structure based on received image data of the target anatomical structure and position data, the position data obtained from a position sensor on the probe, during receiving the image data is to increase the ease of finding the desired scan plane and increase an accuracy of medical diagnosis based on images showing the desired scan plane.

As one embodiment, a method, comprises: outputting to a user, instructions for navigating a medical imaging probe from a current scan position to a next scan position for obtaining a desired scan plane of a target anatomical structure based on received image data of the target anatomical structure and position data, the position data obtained from a position sensor on the probe, during receiving the image data. In a first example of the method, the target anatomical structure includes a target organ and the position data includes a position of the probe on or within a patient relative to a calibrated reference position for an imaging procedure. A second example of the method optionally includes the first example and further includes, wherein the outputting occurs during an imaging procedure and wherein the next scan position corresponds to a next view within a set scan protocol for the imaging procedure. A third example of the method optionally includes one or more of the first and second examples, and further includes, wherein the outputting includes displaying, via a display of an imaging system including the probe, a visual representation of a patient including an indication of a current position of the probe and a target position of the probe to obtain the desired scan plane of the target anatomical structure and/or instructions including a direction and/or distance in which to move the probe relative to the current position of the probe and/or relative to anatomical landmarks on a body of the patient. A fourth example of the method optionally includes one or more of the first through third examples, and further includes, generating an image from the received image data and, for the generated image, determining a corresponding position based on the position data received at the same time as the image data. A fifth example of the method optionally includes one or more of the first through fourth examples, and further includes, detecting a current scan plane of the generated image using a scan plane detection algorithm stored in memory of a controller, where the position data and generated image are inputs into the scan plane detection algorithm, and determining the instructions for navigating the probe based on the detected current scan plane and the desired scan plane. A sixth example of the method optionally includes one or more of the first through fifth examples, and further includes, displaying the generated image via a display during the outputting instructions for navigating the probe. A seventh example of the method optionally includes one or more of the first through sixth examples, and further includes, indicating to a user of the probe that the desired scan plane of the target anatomical feature has been obtained and displaying the generated image including the desired scan plane of the target anatomical feature via the display. An eighth example of the method optionally includes one or more of the first through seventh examples, and further includes, indicating to a user of the probe that there is a mismatch between the detected current scan plane and the determined corresponding position and displaying a request to move the probe to a predetermined reference position to recalibrate the position sensor.

As another embodiment, a method comprises: receiving medical imaging data acquired with an imaging probe; receiving corresponding position data from a position sensor of the imaging probe, the position data acquired at a same time as the medical imaging data; identifying a target anatomical structure and a target scan plane of the target anatomical structure from an image generated with the received medical imaging data and based on the corresponding position data and an image detection framework; and displaying the identified target scan plane of the target anatomical structure via a display. In a first example of the method, receiving the medical imaging data and corresponding position data occurs during an imaging procedure where a user is moving the imaging probe across or within a body of a patient. A second example of the method optionally includes the first example and further includes, at a beginning of the imaging procedure, prior to starting a set scan protocol, directing a user to move the imaging probe to a predetermined reference position and simultaneously acquiring imaging data and position data at the predetermined reference position and further comprising calibrating the position sensor based on the acquired imaging data and position data at the predetermined reference position. A third example of the method optionally includes one or more of the first and second examples, and further includes displaying instructions, via the display, on where and how to move the imaging probe to find the target scan plane of the target anatomical structure, based on a current scan plane and/or anatomical structure identified by the image detection framework based on the generated image and corresponding position data. A fourth example of the method optionally includes one or more of the first through third examples, and further includes continuously receiving medical imaging data and corresponding position data as the imaging probe is moved and updating the displayed instructions based on newly received medical imaging data and position data. A fifth example of the method optionally includes one or more of the first through fourth examples, and further includes displaying the generated image at the same time as displaying the instructions. A sixth example of the method optionally includes one or more of the first through fifth examples, and further includes, wherein the image detection framework includes one or more machine learning algorithms and anatomical structure models stored within a memory of a controller of an imaging system including the imaging probe.

As yet another embodiment, a medical imaging system, comprises: an ultrasound probe including a position sensor; a display; and a controller including non-transitory instructions stored in memory that when executed during operation of the medical imaging system cause the controller to: acquire corresponding image data and position sensor data with the ultrasound probe, as the ultrasound probe is moved during an imaging procedure; automatically detect a desired view including a target scan plane within a target anatomical structure based on an image generated from the acquired image data; verify the detected desired view with the acquired position sensor data; and if there is no mismatch between the acquired corresponding image data and position sensor data, display the detected desired view via the display. In a first example of the system, the instructions further cause the controller to determine, based on the generated image and acquired position sensor data, that the desired view has not been detected and, in response to the desired view not being detected, display, via the display, instructions for how and where to move the ultrasound probe to find the desired view. A second example of the system optionally includes the first example and further includes, wherein the instructions further cause the controller to, if there is a mismatch between the acquired corresponding image data and position sensor data, display, via the display, a request for a user of the medical imaging system to move the ultrasound probe to a predetermined reference position and recalibrate the position sensor. A third example of the system optionally includes one or more of the first and second examples, and further includes, wherein automatically detecting the desired view includes inputting the acquired corresponding image data and position data into a scan plane detection framework including one or more machine learning algorithms and anatomical structure models, where the framework is stored in the memory.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
outputting, to a user during an imaging procedure of a patient carried out according to a set scan protocol, instructions for navigating a medical imaging probe from a current scan position to a next scan position for obtaining a desired scan plane based on received image data of a target anatomical structure of the patient and position data, the position data obtained from a position sensor on the probe, wherein the received image data and the position data are analyzed via a classification model comprising at least one learning algorithm and at least one anatomical model prior to outputting to the user, the desired scan plane dictated by the set scan protocol; and
wherein the position data is relative to at least one of a reference point or a coordinate system identified during calibration of the position sensor, the calibration including identification of a predetermined scan plane or a landmark based on analyzing acquired image data of the patient with one or more image analysis models or frameworks, the acquired image data acquired prior to initiation of the set scan protocol; and
wherein the position sensor is calibrated based on a reference position, the reference position being a position of the probe while imaging the predetermined scan plane or the landmark, the reference position used as one of the reference point or as an origin of the coordinate system.

2. The method of claim 1, wherein the target anatomical structure includes a target organ and the position data includes the position of the probe relative to the reference position, and wherein an anatomic model is calibrated relative to the reference position, the anatomic model representing a spatial orientation of the patient and used to generate the instructions for navigating the probe.

3. The method of claim 2, wherein the outputting occurs during the imaging procedure, wherein the reference position is a first reference position, and wherein the anatomic model is calibrated relative to the first reference position and one or more additional reference positions.

4. The method of claim 1, wherein the outputting includes displaying, via a display of an imaging system including the probe, a visual representation of the patient including an indication of a current position of the probe and a target position of the probe to obtain the desired scan plane of the target anatomical structure and/or instructions including a direction and/or distance in which to move the probe relative to the current position of the probe and/or relative to anatomical landmarks on a body of the patient.

5. The method of claim 1, further comprising generating an image from the received image data and, for the generated image, determining a corresponding position based on the position data received at a same time as the image data.

6. The method of claim 5, further comprising detecting a current scan plane of the generated image using a scan plane detection algorithm stored in memory of a controller, wherein the position data and the generated image are inputs into the scan plane detection algorithm, and determining the instructions for navigating the probe based on the detected current scan plane and the desired scan plane.

7. The method of claim 6, further comprising displaying the generated image via a display during the outputting of the instructions for navigating the probe, wherein outputting the instructions comprises displaying textual instructions for navigating the probe via the display.

8. The method of claim 6, further comprising indicating to the user of the probe that the desired scan plane of the target anatomical structure has been obtained and displaying the generated image including the desired scan plane of the target anatomical structure via a display.

9. A method, comprising:
outputting, to a user during an imaging procedure, instructions for navigating a medical imaging probe from a current scan position to a next scan position for obtaining a desired scan plane based on received image data of a target anatomical structure and position data, the position data obtained from a position sensor on the probe, wherein the received image data and the position data are analyzed via machine learning prior to outputting to the user;
generating an image from the received image data and, for the generated image, determining a corresponding position based on the position data received at a same time as the image data;
detecting a current scan plane of the generated image using a scan plane detection algorithm stored in memory of a controller, wherein the position data and the generated image are inputs into the scan plane detection algorithm, and determining the instructions for navigating the probe based on the detected current scan plane and the desired scan plane; and
indicating to the user of the probe that there is a mismatch between the detected current scan plane and the determined corresponding position and displaying a request to move the probe to a predetermined reference position to recalibrate the position sensor;
wherein the position data is relative to at least one of a reference point or a coordinate system, wherein the at least one of the reference point or coordinate system is independent of the received image data, and wherein the position sensor is calibrated based on the predetermined reference position, the predetermined reference position being a position of the probe relative to a predetermined scan plane identified based on analyzing image data.

10. A method, comprising:
defining at least one of a coordinate system or a reference point;
receiving medical imaging data acquired with an imaging probe;
receiving corresponding position data relative to the at least one of the reference point or coordinate system from a position sensor of the imaging probe, the position data acquired at a same time as the medical imaging data;
identifying a target anatomical structure and a target scan plane of the target anatomical structure from an image generated with the received medical imaging data and based on the corresponding position data via an image detection framework; and displaying the identified target scan plane of the target anatomical structure via a display;

wherein the image detection framework identifies the target anatomical structure and the target scan plane using the received medical imaging data and corresponding position data via at least one machine learning algorithm and at least one anatomical structure model stored within a memory of a controller of an imaging system including the imaging probe; and wherein the position sensor is calibrated based on a landmark identified in the medical imaging data, the landmark used as one of the reference point or as an origin of the coordinate system.

11. The method of claim 10, wherein the receiving the medical imaging data and corresponding position data occurs during an imaging procedure where a user is moving the imaging probe across or within a body of a patient.

12. The method of claim 11, further comprising, at a beginning of the imaging procedure, prior to starting a set scan protocol, directing the user to move the imaging probe to a predetermined reference position and simultaneously acquiring imaging data and position data at the predetermined reference position, and further comprising calibrating the position sensor based on the acquired imaging data and position data at the predetermined reference position.

13. The method of claim 10, further comprising displaying visual instructions, via the display, on where and how to move the imaging probe to find the target scan plane of the target anatomical structure, based on a current scan plane and/or anatomical structure identified by the image detection framework based on the generated image and corresponding position data.

14. The method of claim 13, further comprising continuously receiving medical imaging data and corresponding position data as the imaging probe is moved, and updating the displayed visual instructions based on newly received medical imaging data and position data.

15. The method of claim 13, further comprising displaying the generated image at the same time as displaying the visual instructions, the visual instructions comprising textual instructions.

16. A medical imaging system, comprising:
an ultrasound probe including a position sensor;
a display; and
a controller including non-transitory instructions stored in memory that when executed during operation of the medical imaging system cause the controller to:

acquire corresponding image data and position sensor data with the ultrasound probe, as the ultrasound probe is moved during an imaging procedure, wherein the position sensor is calibrated based on a reference position, the reference position being a position of the ultrasound probe while imaging a predetermined scan plane or a landmark, the predetermined scan plane or landmark identified in the image data;

input the image data and position sensor data into a detection framework;

automatically detect a desired view including a target scan plane within a target anatomical structure based on an image generated from the acquired image data, wherein automatically detecting the desired view comprises inputting the acquired corresponding image data and position data into a classification model comprising at least one learning algorithm and at least one anatomical model;

verify the detected desired view with the acquired position sensor data;

if there is no mismatch between the acquired corresponding image data and position sensor data, display the detected desired view via the display; and prompt a user for confirmation that the image is the desired view.

17. The system of claim 16, wherein the instructions further cause the controller to determine, based on the generated image and acquired position sensor data, that the desired view has not been detected and, in response to the desired view not being detected, display, via the display, instructions for how and where to move the ultrasound probe to find the desired view.

18. The system of claim 16, wherein the instructions further cause the controller to, if there is a mismatch between the acquired corresponding image data and position sensor data, display, via the display, a request for the user of the medical imaging system to move the ultrasound probe to the reference position and recalibrate the position sensor.

19. The method of claim 1, wherein the set scan protocol is a fetal scan protocol and the predetermined scan plane is a transventricular (TV) plane of a fetal head.

20. The method of claim 19, wherein outputting the instructions for navigating the medical imaging probe from the current scan position to the next scan position for obtaining the desired scan plane comprises outputting the instructions for navigating the medical image probe from the current scan position where a mid-sagittal plane of the fetal head is imaged to the next scan position for obtaining a trans-thalamic plane of the fetal head.

* * * * *